US006677361B2

United States Patent
Jacobson et al.

(10) Patent No.: US 6,677,361 B2
(45) Date of Patent: Jan. 13, 2004

(54) TOPICAL FORMULATIONS FOR THE TRANSDERMAL DELIVERY OF NIACIN AND METHODS OF TREATING HYPERLIPIDEMIA

(75) Inventors: Elaine L. Jacobson, Tucson, AZ (US); Myron K. Jacobson, Tucson, AZ (US); Hyuntae Kim, Tucson, AZ (US); Moonsun Kim, Tucson, AZ (US); Jaber G. Qasem, Tucson, AZ (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 09/836,843

(22) Filed: Apr. 16, 2001

(65) Prior Publication Data

US 2001/0049382 A1 Dec. 6, 2001

Related U.S. Application Data

(60) Provisional application No. 60/197,621, filed on Apr. 14, 2000.

(51) Int. Cl.[7] .................. A61K 31/4406; A61K 31/455
(52) U.S. Cl. .................. 514/356; 514/358; 514/824
(58) Field of Search ................... 514/356, 824; 424/484

(56) References Cited

U.S. PATENT DOCUMENTS

| 4,847,260 | A | * | 7/1989 | Abe et al. ............ 514/279 |
| 5,025,026 | A | * | 6/1991 | Osamu ............... 514/356 |
| 5,496,827 | A | | 3/1996 | Patrick ............... 514/310 |
| 5,981,555 | A | | 11/1999 | Kuhrts et al. ........ 514/356 |
| 6,015,821 | A | * | 1/2000 | Horrobin et al. ..... 514/355 |
| 6,337,065 | B1 | * | 1/2002 | Jacobson et al. ..... 424/59 |
| 6,464,992 | B2 | * | 10/2002 | Jacobson et al. ..... 424/401 |
| 6,552,050 | B2 | * | 4/2003 | Jacobson et al. ..... 514/356 |

OTHER PUBLICATIONS

Reinberg et al., Circadian Dosing Time Dependency in the Forearm Skin Penetration of Methyl and Hexyl Nicotinate, 1995, Life Sciences, vol. 57, No. 16, pp. 1507–1513.*

* cited by examiner

Primary Examiner—Frederick Krass
Assistant Examiner—Donna Jagoe
(74) Attorney, Agent, or Firm—Fulbright & Jaworski LLP

(57) ABSTRACT

Niacin and niacin prodrugs are topically administered as suitable formulations to device for impoving the lipid profiles of subjects, preferably humans.

20 Claims, 8 Drawing Sheets

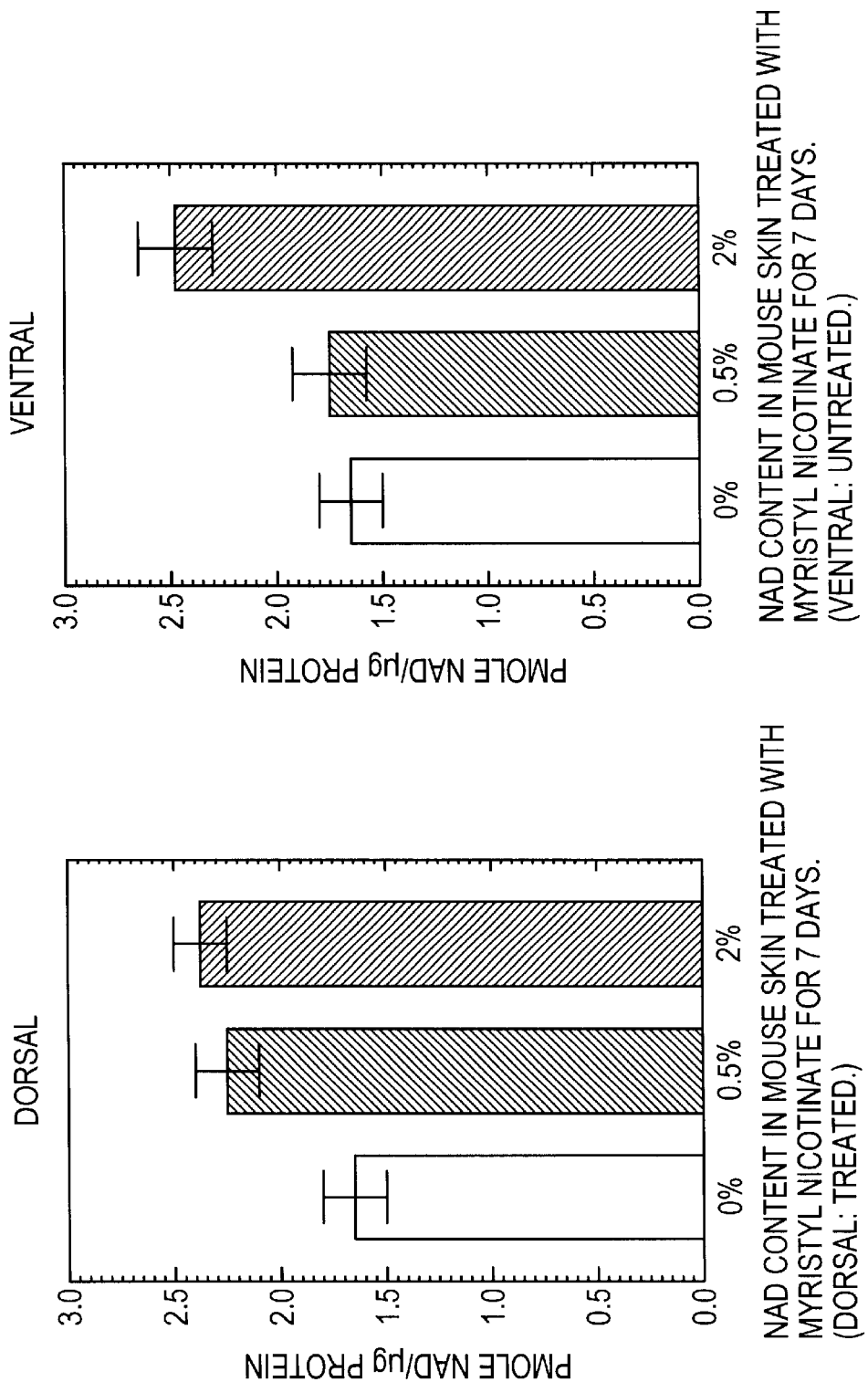

TABLE 1. LIPID RESPONSE TO NIASPAN®

| TREATMENT | N | MEAN PERCENT CHANGE FROM BASELINE TO WEAK 16* | | | | | | |
|---|---|---|---|---|---|---|---|---|
| | | TC | LDL-C | HDL-C | TC/HDL-C | TG | LP(A) | APO B | APO A-1 |
| NIASPAN® 1000mg qhs | 41 | -3 | -5 | +18 | -17 | -21 | -13 | -6 | +9 |
| NIASPAN® 2000mg qhs | 41 | -10 | -14 | +22 | -25 | -28 | -27 | -16 | +8 |
| PLACEBO | 40 | 0 | -1 | +4 | -3 | 0 | 0 | +1 | +3 |
| NIASPAN® 1500mg qhs | 76 | -8 | -12 | +20 | -20 | -13 | -15 | -12 | +8 |
| PLACEBO | 73 | +2 | +1 | +2 | +1 | +12 | +2 | +1 | +2 |

N=NUMBER OF PATIENTS AT BASELINE;

* MEAN PERCENT CHANGE FROM BASELINE FOR ALL NIASPAN® DOSES WAS SIGNIFICANTLY DIFFERENT (P<0.05) FROM PLACEBO FOR ALL LIPID PARAMETERS SHOWN EXCEPT APO A-1 AT 2000mg.

FROM PHYSICIANS' DESK REFERENCE, 53 EDITION, P1505-1506, 1999.

*FIG. 2*

TABLE 2. MEAN STEADY-STATE PHARMACOKINETIC PARAMETERS FOR PLASMA NIACIN

| NIASPAN® | | NIACIN | |
|---|---|---|---|
| DOSE/DAY | GIVEN AS | PEAK CONCENTRATION (µg/ml) | TIME TO PEAK (HRS) |
| 1000mg | 2 X 500mg | 0.6 | 5 |
| 1500mg | 2 X 750mg | 4.9 | 4 |
| 2000mg | 2 X 1000mg | 15.5 | 5 |

FROM PHYSICIANS' DESK REFERENCE, 53 EDITION, P1505-1506, 1999.

FIG. 3

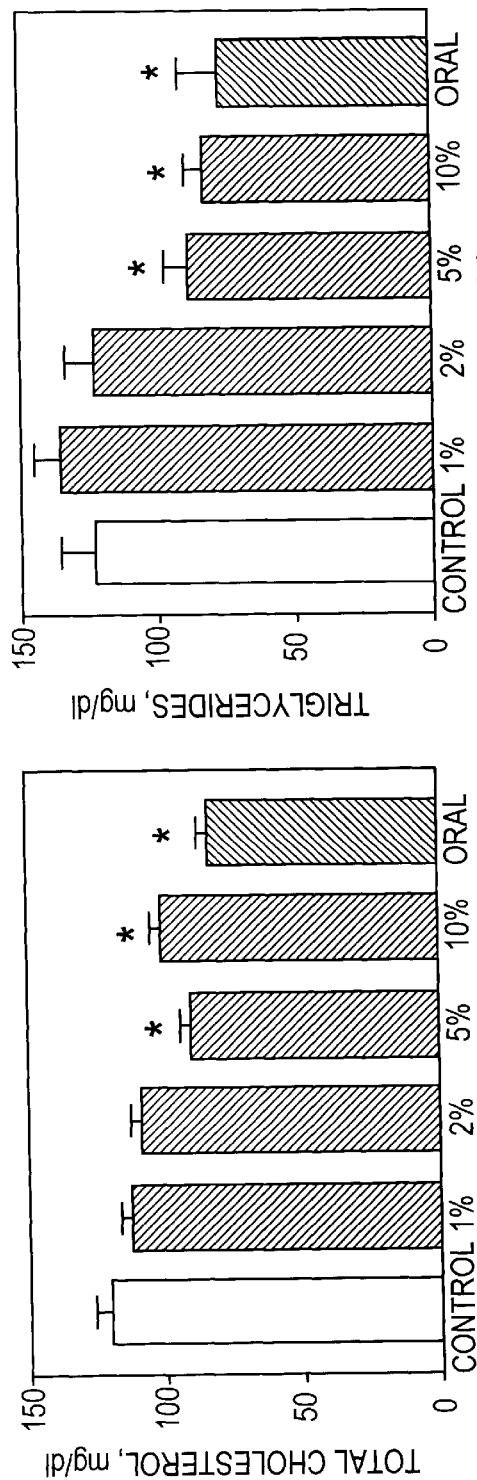

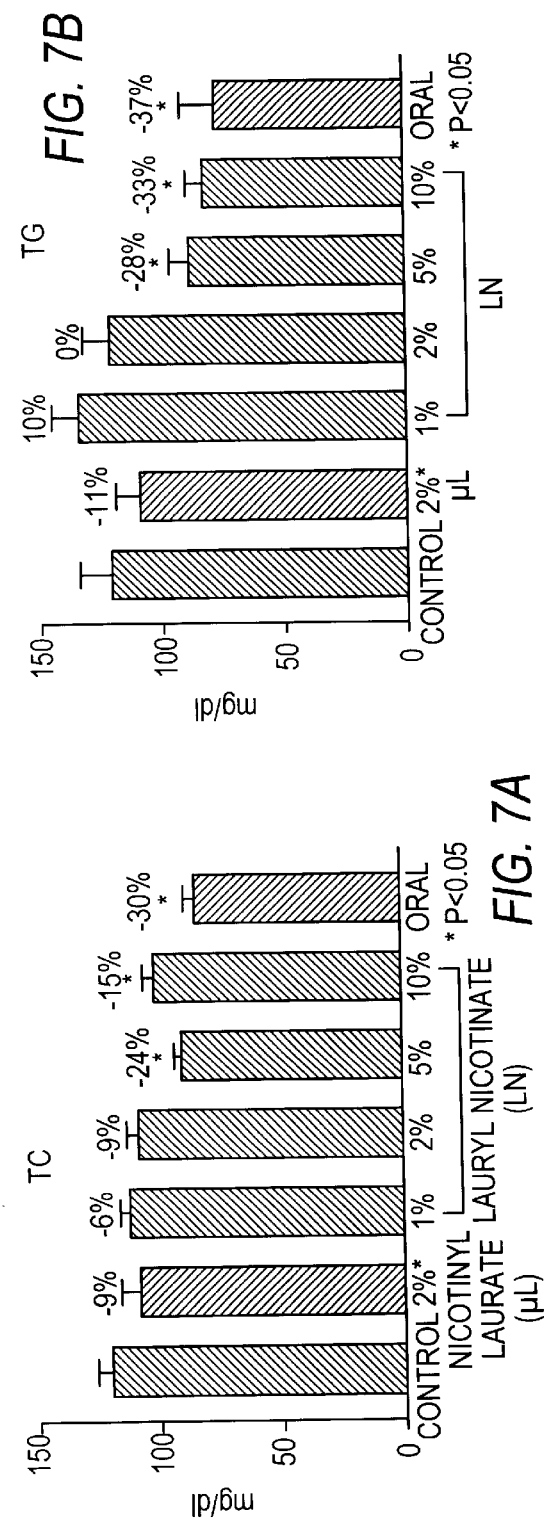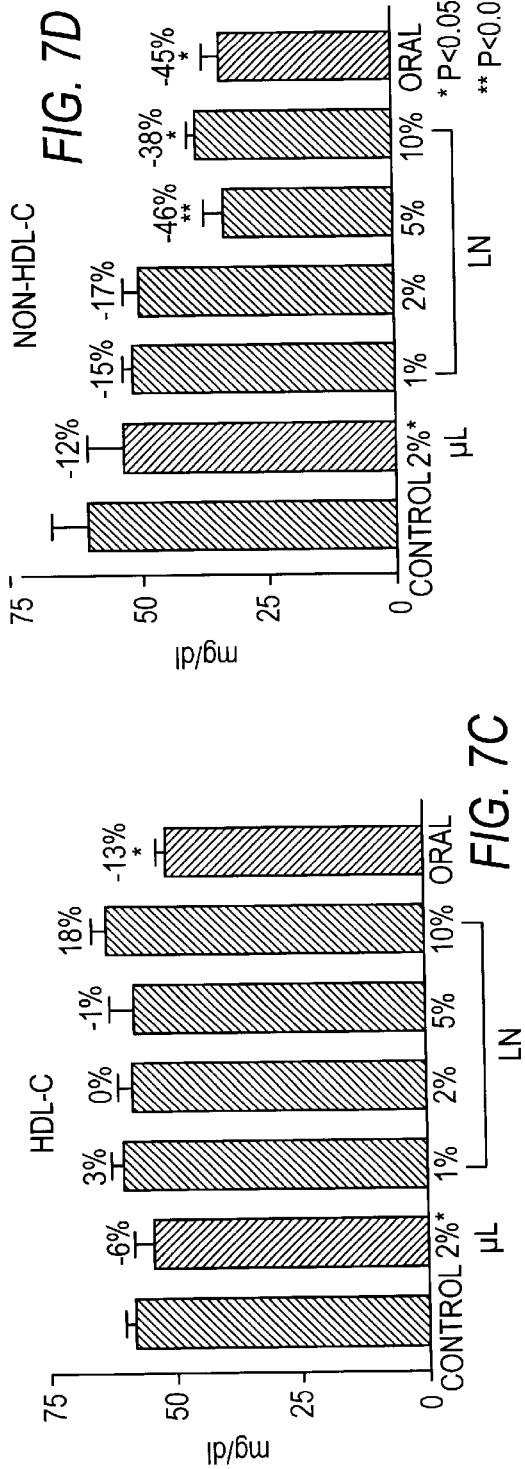

TOPICAL FORMULATIONS FOR THE TRANSDERMAL DELIVERY OF NIACIN AND METHODS OF TREATING HYPERLIPIDEMIA

This application claims the benefit of Provisional Application Ser. No. 60/197,621 filed Apr. 14, 2000.

FIELD OF THE INVENTION

This invention relates to topical formulations for transdermal delivery of niacin and esters and alcoholic fatty-acid esters as described herein derivatives thereof and the transdermal treatment of hyperlipidemia and hypercholesterolemia with these agents. Therapeutic uses of the system are also described. The topical formulations are useful for, e.g., treating hyperlipidemia in a mammal.

Hyperlipidemia and hypercholesterolemia are conditions that have a well established correlation with increased risk of other conditions, such as heart attacks, atherosclerosis, and other deleterious ailments. There are numerous agents available for lowering cholesterol and lipid levels, including gemfibrizol, probucol, and, more recently, the "statins" e.g, lovastatin.

Niacin (nicotinic acid), a water soluble B-complex vitamin, is used orally for the treatment of hyperlipidemia and has been shown to be effective in reducing total plasma cholesterol (C), low density lipoproteins LDL-C and very low density lipoprotein triglycerides (VLDL-triglycerides), all of which are associated with health risks, while raising serum levels of high density lipoproteins (HDL-C) which are considered a "healthy" lipoprotein, in patients with type II, III, IV, and V hyperlipoproteinemia.

Although the mechanism by which niacin alters lipid profiles has not been well defined, its mechanisms of action have been shown to include inhibition of free fatty acid release from adipose tissue (see Carlson, L. A., Froberg, S. O. and Nye, E. R., Nicotinic acid in the rat. 11. Acute effects of nicotinic acid on plasma, liver, heart, and muscle lipids, Acta Med Scand 180: 571–579, 1966), and increased lipoprotein lipase activity (see Priego, J. G., Pina, M., Armijo, M., Sunkel, C. and Maroto, M. L., Action of etofibrate, clofibrate and nicotinic acid on the metabolism of lipids in normolipemic rats. Short term effects and method of action, Arch Farmacol Toxicol 5: 29–42, 1979). More than 14 million Americans have elevated blood LDL-C levels. HMG-CoA reductase inhibitors (statins) are the most widely used class of drugs for treating patients with elevated levels of LDL-C. Niacin, however, is the only drug recommended by the American Heart Association for HDL improvement in primary prevention of cardiovascular diseases in addition to lowering LDL-C. Niacin therapy is not only very cost-effective as a monotherapy but it also is beneficial as a combination therapy because it complements the effects of other classes of lipid-lowering drugs. Niacin is a second or third choice for isolated, hypercholesterolemia because of a high incidence of side effects associated with oral niacin therapy. However, it has a therapeutic advantage as a monotherapy when reduction of both LDL-C and triglycerides are desired such as for patients with severe combined hyperlipidemia. Niacin can also be used in combination with other cholesterol-lowering agents such as the "statins" to maximize lipid-lowering activity. One study shows that a niacin/lovastatin combination is highly effective in lowering LDL-C, triglycerides and lipoprotein a[Lp(a)] while retaining niacin's potency in raising HDL-C (Kashyap, M. L., Evans R., Simmons, P. D., Kohler, R. M. and McGoven, M. E., New combination niacin/statin formulation shows pronounced effects on major lipoproteins and well tolerated, J Am Coll Card Suppl. A 35: 326, 2000).

Niacin has been widely used for reducing serum cholesterol levels because it is considered a cost-effective therapy. In oral doses of 2 to 3 g daily, it reduces levels of total and LDL-C by an average of 20% to 30%, reduces triglyceride levels 35% to 55%, increases HDL-C 20% to 35%, and reduces Lp(a) in humans. Niacin also reduces total mortality as well as mortality from coronary artery disease (see The Coronary Drug Project Research Group, JAMA 231: 360–381, 1975; and Canner, P. L., Berge, K. G., Wenger, N. K., Stamler, J., Friedman, L., Prineas, R. J. and Friedewald, W., Fifteen year mortality in Coronary Drug Project patients: long-term benefit with niacin, J Am Coll Cardiol 8: 1245–1255, 1986.) and it helps to slow or reverse the progression of atherosclerosis (see Blankenhorn, D. H., Nessim, S. A., Johnson, R. L., Samnarco, M. E., Azen, S. P. and Cashin-Hemphill, L., Beneficial effects of combined colestipol-niacin therapy on coronary atheroscloerosis and coronary venous bypass grafts, JAMA 257: 3233—3240, 1987.; and Cashin-Hemphill L.; Mack, W. J., Pogoda, J. M., Samnarco, M. E., Azen, S. P. and Blankenhorn, D. H., Beneficial effects of colestipol-niacin on coronary atherosclerosis. A 4-year follow-up, JAMA 264: 3013–3017, 1990).

Oral niacin therapy has side effects that limit its utility. Although niacin is a vitamin, it must be used in therapeutic doses to lower cholesterol. At these doses, both immediate-release and sustained-release niacin can have several side effects. The most common side effect of niacin is flushing, a warm feeling in the skin usually associated with redness and sometimes itching. Flushing is not dangerous but most patients find it very uncomfortable, which seriously limits patient compliance with therapy. Niacin-induced flushing can be substantially attenuated by pretreatment with cyclooxygenase inhibitors, suggesting that the vasodilation is caused by a prostaglandin-mediated mechanism (see Carlson, L. A., Nicotinic acid and inhibition of fat mobilizing lipolysis. Present status, of effects on lipid metabolism, Adv Exp Med Biol 109: 225–23 8, 1978).

Liver function tests are always monitored in patients taking niacin since elevation of serum transaminase levels has been associated with niacin treatment, and sustained-release niacin formulations have been associated with more serious liver problems (see McKenney, J. M., Proctor, J. D., Harris, S., and Chinchili, V. M., A comparison of the efficacy and toxic effects of sustained- vs immediate-release niacin in hypercholesterolemic patients, JAMA 271: 672–777, 1994; and Stafford, R. S., Blumenthal, D. and Pasternak, R. C., Variations in cholesterol management practices of U.S. physicians, J Am Coll Cardiol 29: 139–146, 1997). Other possible side effects of oral niacin therapy include activation of peptic ulcers, gout, and worsening of diabetes control. Given the potential for side effects, oral niacin therapy requires careful clinical monitoring.

The pharmacokinetic profile of niacin taken orally is complex due to rapid and extensive first-pass metabolism, resulting in a nonlinear relationship between niacin dose, thus there is no correlation between the lipid parameters and plasma niacin levels. For example, data show that Niaspan® doses of 1,000 mg results in an improvement in lipid profiles with barely detectable increases in plasma niacin (see Physicians Desk Reference, 53rd edition, p 1505–1506, 1999). Niaspan® is an extended release niacin formulation approved by the FDA for the treatment of hypercholesterolemia and hypertriglyceridemia (Capuzzi, D. M., Guyton, J. R., Morgan, J. M., Goldberg, A. C., Kriesberg, R. A., Brusco, O. A. and Brody, J., Efficacy and safety of an extended-release niacin (Niaspan): A long term study, *Am J Cardiol* 82: 74u–8 I u, 1998; and Morgan, J. M., Capuzzi, D. M., and Guyton, J. R., A new extended-release niacin (Niaspan): Efficacy, tolerability, and safety in hypercholesterolemic patients, *Am J Cardiol* 82: 29u–34u, 1998). Thus, significant improvement in the serum lipid profile can be achieved without a dramatic increase in nicotinic acid plasma levels after the oral administration of niacin (see Knopp, R. H., Alagona, P., Davidson, M., Goldberg, A. C., Kafonek, S. D., Kashyap, M., Sprecher, D., Superko, H. R., Jenkins, S., Marcovina, S., Equivalent efficacy of a time-release form of niacin (Niaspan) given once-a-night versus plain niacin in the management of hyperlipidemia, *Metabolism* 47: 1097–104, 1998). This demonstrates that sustained elevation of blood levels of niacin is not required to achieve a therapeutic effect. Indeed, the data support the argument that tissue saturation with niacin appears to be the key factor in obtaining therapeutic benefit. Prolonged low-level exposure via controlled release oral formulations is preferable to the high level, short exposures resulting from immediate release formulations because it avoids inconvenient dosing regimens and reduces unpleasant side effects. However, controlled release oral formulations of niacin still show significant degree of flushing and hepatic dysfunction. In view of the pharmacokinetic fate of oral niacin, the ideal method of niacin administration has yet to be achieved.

Transdermal drug delivery is an attractive route due to the controlled input of these agents and avoidance of the hepatic first-pass effect. However, it is unlikely that hydrophilic compounds such as niacin will easily permeate across the skin. We demonstrate in the present study that the chemical modification with fatty alcohols allows niacin to permeate the skin in a controlled manner for systemic delivery and to affect the blood lipid profile in animal models. Both chemical and enzymatic hydrolysis of prodrug esters of niacin have been extensively evaluated using human and rat plasma and hog liver carboxylesterase preparations described by Wernly-Chung, G. N., Mayer, J. M., Tsantili-Koulidou, A. and Testa, B., Structure-reactivity relationships in the chemical hydrolysis of prodrug esters of nicotinic acid, *Int J Pharma* 63: 129–134, 1990. The studies show that chemically stable niacin esters are excellent substrates of esterases. A study indicates that the binding of niacin esters mainly depends on lipophilicity (optimal log $P_{oct/w}$=2.3) and steric factors. Niacin esters up to hexyl nicotinate are commercially available.

Transdermal delivery systems are a convenient and effective alternative for the administration of many types of medications, including anti-anginals (nitroglycerin), hormones (estrogens) and antihypertensives (cloncidine). Transdermal delivery is beneficial because the agents are delivered directly into the blood stream, avoiding first-pass metabolism in the liver, so that drug delivery is continuous and sustained. Transdermal delivery also provides a sustained and consistent delivery of medication, avoiding peaks and valleys in blood levels which are often associated with oral dosage forms and which are usually undesirable. Thus, using transdermal delivery, one can administer lower doses of drug to achieve the same therapeutic effect compared to oral administration, reducing or eliminating dose-dependent side effects.

Preparing suitable formulations of medications is a challenging task, and many hurdles must be overcome to achieve a suitable topical dosage form. The skin, which has protective layers designed to prevent penetration of foreign matter, must be sufficiently penetrated to provide the active agent to the desired site for absorption into the bloodstream. Skin is a complex organ system, consisting of multiple layers. The uppermost, or "stratum corneum" layer of skin consists of non-living material derived primarily from the terminal differentiation of epidermal keratinocytes, and provides a protective barrier for the underlying components of skin. The epidermis contains a number of cell types, although keratinocytes are the major cell type. Dermal fibroblasts are embedded within a matrix comprised of collagen, elastin, proteoglycans, and other extracellular matrix molecules. Blood capillaries are found in the dermis, but the epidermis is non-vascular.

Additionally, the drug itself must be suitable for administration. The size of a drug molecule, its charge, and polarity are factors that contribute to the ability of the agent to penetrate the skin to the desired site or to blood vessels for systemic distribution.

The benefits of transdermal delivery indicate that transdermal delivery systems of niacin for, e.g, the treatment of hyperlipidemia or vitamin therapy are desirable.

It is an object of the present invention to provide transdermal delivery formulations and systems for the systemic delivery of niacin to a patient, e.g., a mammal such as a human, wherein the niacin is provided in a pro-drug of niacin, e.g., nicotinic acid esters and fatty acid esters of the corresponding alcohol. These are referred to herein as "pro-niacin".

It is also an object of the invention to treat hyperlipidemia and hpercholesterolemia via transdermal delivery of niacin using pro-niacin esters.

These and other objects of the invention are achieved by the present invention which is described in the following disclosure.

BRIEF DESCRIPTION OF THE FIGURES

FIG. 1 is depicts the NAD content in mouse skin treated with myristyl nicotinate for 7 days vs. untreated skin;

FIG. 2 is a table showing lipid response to Niaspan®;

FIG. 3 is a table of the mean steady-state pharmacokinetic parameters for plasma niacin;

FIGS. 6a–d is a graph showing the effect of oral niacin and transdermal lauryl niacin on the lipid profiles of apoB/CETP transgenic mice.

FIG. 7 is a graph showing the effect of nicotinoyl laurate compared to the results shown in FIG. 6.

DETAILED DESCRIPTION OF PREFERRED EMBODIMENTS

Figure 4A:
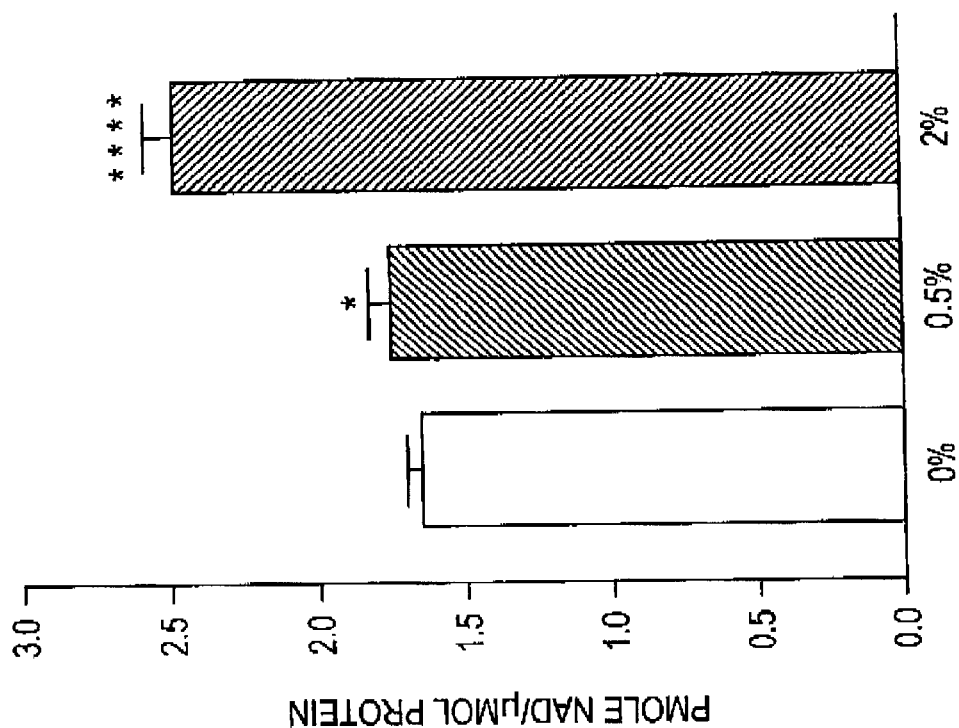
FIGS. 4a and 4b are graphs comprising NAD content in mouse skin treated with myristal niacin for 7 days (4a) vs. untreated skin (4b)

Transdermal delivery is an attractive alternative route of niacin administration that circumvents toxic first-pass hepatic actions. The topical delivery system of invention takes into account the partitioning of niacin through the stratum corneum which is at least partly controlled by the esterification of niacin or addition of a fatty acid to form a nicotinyl compound, collectively the pro-niacins of the present invention, such as those sown in FIG. 7. The rate and site of metabolic conversion of the pro-niacin contribute to penetration of the skin and to systemic absorption into the blood vessels in the lower skin layers. The primary consideration for transdermal delivery of many hydrophilic drugs such as niacin is the high diffusional resistance of the intact stratum corneum. Molecular modification of niacin the drug, more commonly in the form of a prodrug, circumvents this problem.

Niacin pro-drugs, e.g., nicotinic acid esters are preferred over nicotinic acid because they provide prodrugs with highly desirable formulation properties for transdermal delivery. Additionally, conversion to niacin by esterases present in skin provides sustained release of the active ingredient. The C10–C18 esters of niacin are particularly preferred, although suitable formulations can be prepared with C1 to C22 nicotinic acid esters. The niacin esters and nicotinyl compounds may be straight chain or branched, substituted or unsubstituted provided the total number of carbons meets the criteria set forth herein.

It is preferred that the compositions comprise from 1 to 30% by weight of the niacin prodrug, preferably 1–20%, and most preferred 1–10%.

The niacin or niacin prodrug preferably has a log P of from 0.5 to about 12, 4.5 to 10, most preferably from 4.8 to 9.7 when measured using water/octanol partitioning.

To evaluate the efficacy of transdermal delivery, a hairless mouse model and an apoB/CETP double transgenic mouse model was used. The apoB/CETP model provides a suitable model of human lipid metabolism as these mice are known to display a lipoprotein cholesterol distribution most similar to that of normolipidemic humans. Transgenic mice expressing specific human genes have been widely used to investigate the lipid metabolism and to test potential hypolipidemic drugs, providing the potential for better prediction of the human response. Transgenic mice expressing both human apoB100 and human CETP show a human-like serum HDL-C/LDL-C distribution and are commercially available. ApoB100 is a protein component of VLDL and LDL, and it is the ligand responsible for binding to the LDL receptor, whereas CETP mediates the distribution of lipids among different classes of lipoproteins. The lipoprotein cholesterol profile of the double transgenic mice is significantly different from that of nontransgenic, human apoB single transgenic and CETP single transgenic mice, in which most of the cholesterol is found in the HDL fractions. The apoB100/CETP double transgenic mice display the lipoprotein cholesterol distribution most similar to that of normolipidemic humans (i.e., a ratio of LDL-C to HDL-C of approximately 2 to 1) when fed a normal chow diet described by Grass, D. S., Sainai, U., Felkner, R. H., Wallace, R. E., Lago, W. J. P., Young, S. G. and Swanson, M. E., Transgenic mice expressing both human apolipoprotein B and human CETP have a lipoprotein cholesterol distribution similar to that of normolipidemic humans, *J Lipid Res* 36: 1082–1091, 1995.

The topical formulations of the present invention can be used to lower cholesterol and/or lipids in a patient in need thereof, mammals and humans, by applying a sufficient amount of a transdermal formulation containing a sufficient, i.e. therapeutically effective amount of niacin pro-drug in a suitable topical base to the skin of a subject to reduce serum cholesterol and/or lipid levels of LDL, VLDL's, or to increase serum HDL levels. Thus, the formulations may be used to prevent hyperlipidemia and hypercholesterolemia, or to treat those conditions.

EXAMPLES 1 AND 2—PREPARATION OF NIACIN ESTERS

Example 1

Nicotinic acid esters were prepared by treating nicotinyl chloride with triethylamine (TEA), dimethylaminopyridine (DMAP) and various $C_1$ to $C_{18}$ alcohols under nitrogen (all chemicals obtained from Sigma Aldrich). The resultant esters were separated by silica gel column chromatography and converted to their respective HCl salts for further purification. Thin layer chromatography (TLC) and $I_H$-NMR confirmed the purity and identity of the final products listed in Table 1 below. Examinations by TLC were performed on Analtech Uniplate silica gel GF plates. Column chromatographic purifications were done with silica gel (Merck, 60 A, 230–400 mesh for flash chromatography).

Example 2

Female hairless mice (HRS-J. 6–8 weeks old were used.) These were housed in solid bottom cages provided with sterile feed and water and lithium, with a 14:10 light-dark cycle. The nicotinic acid esters of Example 1 were applied with a gloved finger daily to the backs of hairless mice in 200 mg of Vanicream Lite™ skin care lotion (Pharmaceutical Specialties, Inc., containing purified water, white petrolatum, ceteareth alcohol and ceteareth-20, propylene glycol, sorbitol solution, simethicone, glyceryl monostearate, polyethylene glycol monostearate, sorbic acid and BHT) at concentrations in the range of 0.5 to 2.0% (wt/wt) for one week. Control mice received 200 mg of the lotion alone. The animals were euthanized by cardiac injection of pentobarbital prior to skin excisions. Dorsal and ventral skin samples were immediately frozen in liquid nitrogen and stored at –80° C.

Since niacin is converted to NAD in tissue, NAD content was used as a marker of niacin saturation (Fu, C. S., Swenseid, M. E., Jacob, R. A. and McKee, R. W., Biochemical markers for assessment of niacin status in young men: levels of erythrocyte niacin coenzymes and plasma tryptophan, *J Nutrition* 119: 1949–195 5, 1989). The systemic transdermal delivery of niacin was assessed by determining the NAD content of a skin site that is remotely located from the site of topical application. Demonstration of tissue saturation of niacin using a transdermal delivery system according to the invention is shown in FIG. 1, which shows treatment with myristyl nicotinate.

For NAD and protein analyses, the tissue was homogenized using a Polytron in 1 ml of ice-cold 0.5 M $HClO_4$ and centrifuged at 3,000 rpm for 15 min. The supernatant was neutralized with ice-cold 2 M KOH/0.66 M $KH_2PO_4$ for the NAD assay. The pellet was dissolved in 1 ml of 0.1 M NaOH for protein assay. NAD content was assessed based on the principle of enzymic cycling (Jacobson, E. L. and Jacobson, M. K., Tissue NAD as biochemical measure of niacin status in humans, *Methods Enzymol* 280: 221–230, 1997). The BCA method (Pierce Chemical Co.) was employed for protein determination. Determination of $P_{oct/w}$ was conducted using the reversed-phase HPLC method as reported by Harnisch M., Mokel H., Relationship between Log Pow shake-flask values and capacity factors derived from revesed-phase high-performance liquid chromatography for n-alkyl benzenes and some OECD reference substances. *J. Chrom,* 282, (315–332), 1983. Results are shown in Table 1.

TABLE 1

Properties of Niacin Prodrugs

| Alkyl Carbon Chain Length | Log P Value* | Erythematous Response |
|---|---|---|
| 1 carbon | 0.84 | Yes |
| 2 carbons | 1.3 | Yes |
| 4 carbons | 2.4 | Yes |
| 6 carbons | 3.5 | Yes |
| 8 carbons | 4.8 | Yes |
| 10 carbons | 5.8 | Slight |
| 12 carbons | 6.6 | No |
| 13 carbons | 7.5 | No |
| 14 carbons | 7.6 | No |
| 15 carbons | 8.3 | No |
| 16 carbons | 9.2 | No |
| 18 carbons | 9.7 | No |

*Determined as described in Harnisch and Mokel, supra.

The results summarized in Table 1 supra show that nicotinic acid esters with log P values between about 6.0 and about 8.0 are the preferred compounds for transdermal delivery of niacin to achieve tissue saturation, since esters with log P values of less than about 6, including C1 to C8 esters, cause erythematous response, while esters with log P values greater than 6 do not. The C10 ester showed reduced erythematous response compared to C8 or lower esters.

Example 3

Esters of niacin were also synthesized according to known methods described by Ono, N., Yamada, T. Saito, T. Tanaka, K. and Kaji, A., A convenient procedure for esterification of carboxylic acids, Bull. Chem. Soc. Jpn. 51:2401–2404, 1978. The treatment of niacin with various alkyl bromide and 1,8-diazbicyclo[5,4,0]undec-7-ene (DBU) in benzene under nitrogen resulted in esters that could be separated by silica gel column chromatography. The purity and identity of the final products were confirmed by TLC, $^1$H-NMR spectroscopy, reversed-phase HPLC, and elemental analysis. Niacin, DBU and all the alkyl bromides were purchased from Sigma-Aldrich. Examinations by TLC were performed on Analtech Uniplate silica gel GF plates. Column chromatographic purifications were done with silica gel (Merck, 60 A, 230–400 mesh for flash chromatography). $^1$H-NMR spectra were recorded on a Varian Gemini-300 NMR spectrometer using tetramethylsilane as the internal reference.

Example 4

Figure 4B:
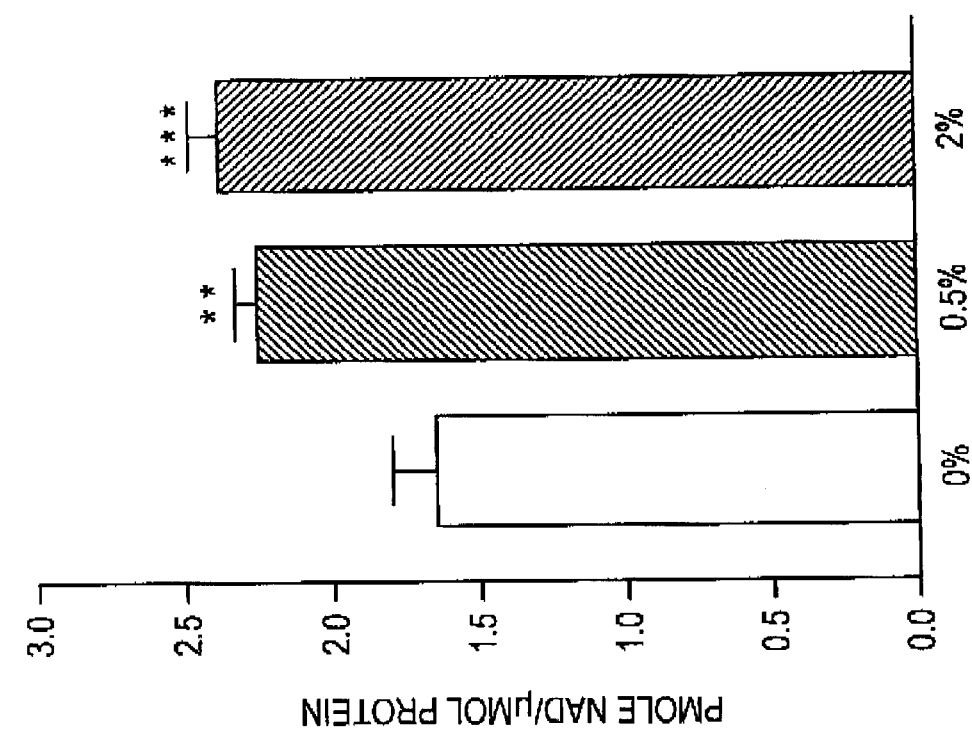
Figure 5:
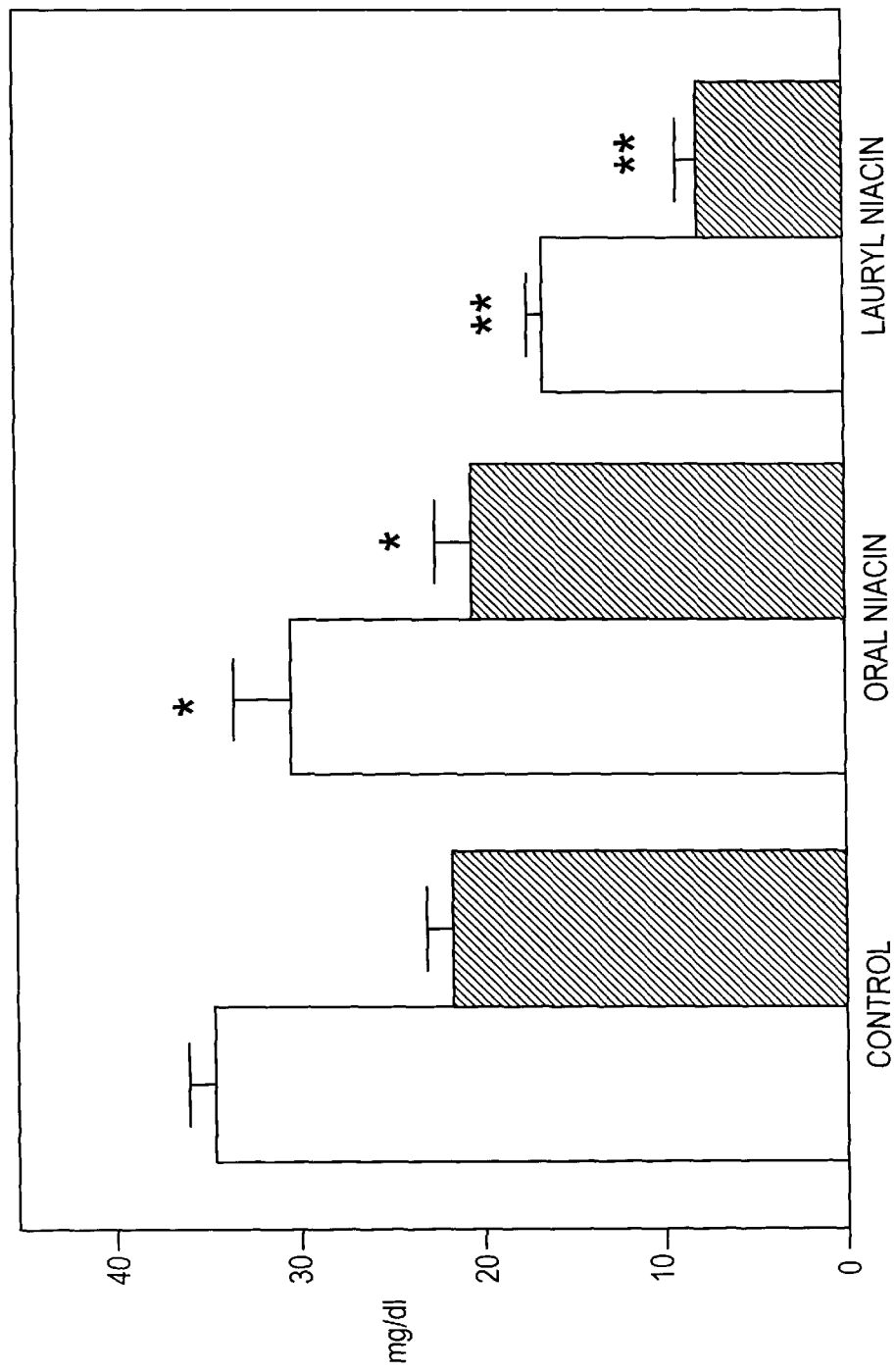
FIG. 5 is a graph showing the cholesterol lowering effects of transdermal lauryl niacin ester vs. oral niacin in hairless mice against a control.
Figure 8:
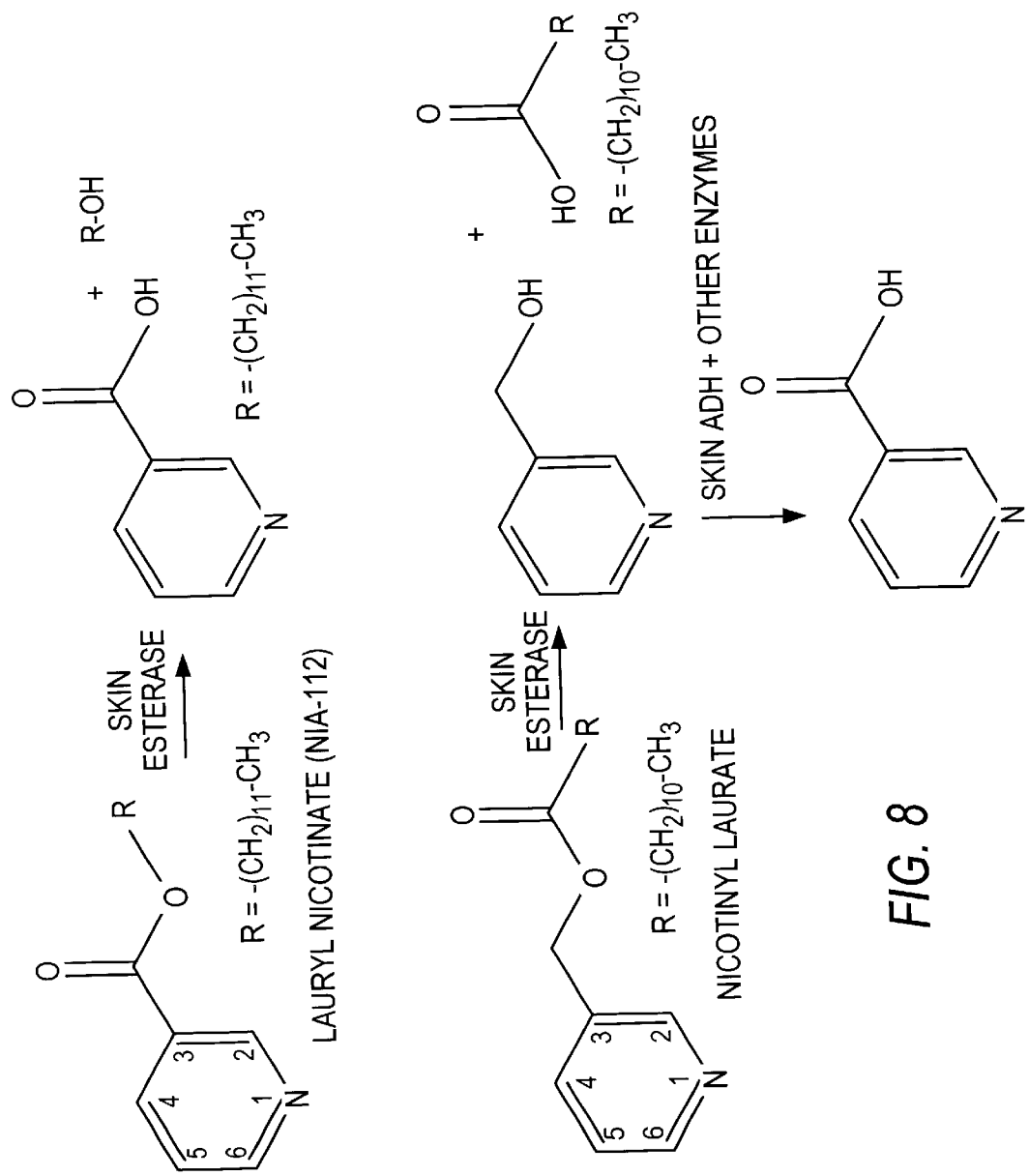
FIG. 8 show the general chemical structures of nicotinate and nicotinyl compounds suitable for use with the present invention.

Lauryl niacin esters prepared according to Example 3 was evaluated in hairless mice using the procedure set forth in Example 2 except that concentrations of 1 to 10% wt/wt. lauryl niacin ester were used. NAD and protein determination were conducted as described in Example 2, and the results are shown in FIGS. 4a and 4b.

Additionally, a plasma lipid analysis was performed by taking fasting (16 h) blood samples of the hairless mice were obtained at the beginning, at 30 days and 60 days from the retroorbital plexus, and at the end of treatment by cardiac puncture. The animals were euthanized by cardiac injection of pentobarbital prior to blood collection. Blood was collected into microfuge tubes containing 10 μl of heparin, plasma separated by centrifugation at 2,000×g for 15 minutes and stored at −80° C. until analysis within 1 week. Total cholesterol, HDL-C and triglycerides were measured enzymatically, using a clinical chemistry analyzer Syncrhon CX7 by Beckman). Results are shown in FIGS. 4a and 4b.

Example 5

Female apoB/CETP double transgenic mice (Taconic Biotechnology, Germantown, N.Y.) were divided into 6 groups and housed in groups of 6 animals per. The lauryl ester was used as a 5% lotion formulation and applied to the shaved backs of the test animals receiving a standard diet, 5 times a week for 4 weeks. For oral administration, niacin (sodium salt) was dissolved in drinking water at a concentration of 0.75% (0.63% as free acid). Niacin intake was estimated from the water consumed. The estimated daily niacin intake was approximately 1,400 mg/kg.

The oral dose used was 760 mg/kg/day and the topical dose was 250 mg/kg/day as niacin. The oral niacin dose chosen is in the range of 500 to 900 mg/kg/day typically used in preclinical rodent studies described by Santos, K. F. R., Oliveira, T. T., Nagem, T. J., Pinto, A. S. and Oliveira, M. G. A., Hypolipidaemic effects of naringenin, rutin, nicotinic acid and their associations, Pharmacol Res 40, 493–496, 1999. The oral dose, on the basis of body surface area, is equivalent to a human dose of 3.7 g/day, while the topical dose is equivalent to 1.2 g/day.

For topical administration, niacin lauryl esters was applied daily to the shaved backs of mice in 200 mg of lotion at concentrations of 1, 2, 5 and 10% (wt/wt) for 13 weeks. Per 25-g mouse, the daily topical doses would be in the range of 34 to 340 mg/kg as niacin. Control mice received equal amounts of the vehicle lotion alone. A lipid analysis was performed as described in Example 4. Results are shown in FIGS. 6a–d.

Improvement of lipid profiles of apoB100/CETP transgenic mice treated with niacin prodrug. The effect of transdermal delivery of lauryl niacin ester on plasma lipid profiles in a comparison with oral niacin in the apoB100/CETP double transgenic mice for 90 days. A total of six groups of six animals were used in this study. For topical administration, lauryl niacin ester was applied daily to the shaved backs of mice. For oral administration, niacin (sodium salt) was dissolved in the drinking water. After 90 days, the topical treatment at one-fourth the dose of the oral treatment lowered total cholesterol, triglycerides, and the LDL-C fraction by 15, 33 and 38% while HDL-C was elevated by 8%. The oral treatment lowered total cholesterol, triglycerides, LDL, and HDL-C fractions by 29, 37, 45% and 13%, respectively. These results show that lauryl nicotinate can be highly effective as a transdermal therapeutic for positively modulating serum lipid profiles.

The results show that the topical treatment lowered total plasma cholesterol level by 52%, whereas oral niacin lowered total cholesterol by 12%.

The results show niacin pro-drugs, e.g., niacin esters, can be applied dermally as a prodrug to control blood lipid imbalance as an alternative to oral niacin that circumvents flushing and potentially toxic first-pass hepatic effects. The results show that the topical treatment lowered total plasma cholesterol level by 52%, whereas oral niacin lowered total cholesterol by 12%.

The myristyl- and lauryl esters of niacin show no cutaneous vasodilation, indicating that niacin prodrugs can be made without such an undesirable effect. They provide prodrugs with highly desirable formulation properties for transdermal delivery and conversion to niacin by esterases present in skin will provide a sustained release of the active ingredient without vasodilation for optimum systemic delivery. The results in animal models strongly suggest that the transdermal approach can be successfully applied to the overall improvement of lipid profiles by niacin administration, in humans or other mammals.

Niacin and nicotinic acid esters and nicotinyl compounds of the present invention penetrate and saturate tissue when administered to a subject, and as discussed above, tissue saturation is related to reduction in serum cholesterol and lipid levels showing transdermal delivery of niacin, particularly in ester form, will effectively reduce serum LDL and VLDL levels and/or increase serum HDL levels.

The nicotinic acid esters are suitable for transdermal delivery, particularly C10 or greater esters, e.g., C10–C18 and most preferably C12–C16. However, suitable formulations can be prepared with C8 or lower esters, and they are included within the scope of the invention. Corresponding nicotinyl compounds are also effective.

In addition to creams and lotions, topical formulations such as shampoos, liquids such as eye washes, balms and sticks such as lip balms and deodorant sticks, soaps, patches, bandages, suturing threads, coated implant devices, and any other type of system designed for topical application. Suitable pharmaceutical vehicles will be used to prepare the transdermal formulations of the invention, including petrolatum, whitepsol ointment, various lotions, emulsion bases, creams, and the like.

Most preferred is a transdermal delivery system. Suitable transdermal delivery systems (patches) for delivery of nicotine are known in the art, such as those described in U.S. Pat. No. 4,839,174; 4,943,435; and 5,016,652. Many other examples of these types of devices are known in the art. Typical transdermal systems include a reservoir or matrix containing the drug, and an adhesive layer which is permeable to the active agent, in this case niacin and more preferably nicotinic acid esters. An adhesive layer, which may be the same as the permeable layer, adheres to the skin of a subject, allowing the agent to be released and absorbed into the skin for subsequent systemic circulation and distribution to other tissue. In operation, the device will transdermally deliver a sufficient dose of niacin or nicotinic acid ester to deliver a sufficient amount of niacin to saturate the tissue of the subject with niacin, and to provide a reduction in total cholesterol, VLDL, or LDL levels and/or an increase or improvement in HDL levels. Improvements in total cholesterol are conveniently expressed as a lowering of the ratio of total cholesterol:HDL or LDL:HDL. The result show that transdermal delivery of the compounds described herein produce improvements in the cholesterol and lipid profiles of the subjects similar to those known to be produces with oral niacin therapy.

Other features of the invention will be clear to the skilled artisan and need not be set forth herein.

All references cited herein are incorporated by reference in their entireties.

We claim:

1. A method of lowering serum triglyceride in a subject in need thereof comprising topically administering to said subject an amount of a compound of formula

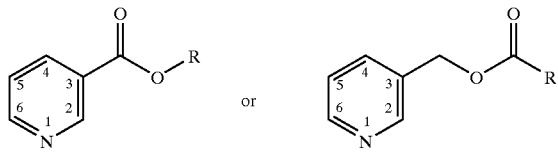

wherein, in each compound R is C1–C22 alkyl, in an amount sufficient to reduce serum triglyceride in said subject.

2. The method of claim 1, wherein R is C10–C18 alkyl.

3. The method of claim 1, wherein said compound is

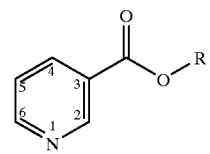

wherein R, is C1–C22 alkyl.

4. The method of claim 1, wherein said compound is

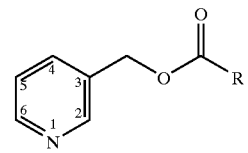

wherein R is C1–C22 alkyl.

5. The method of claim 1, wherein said compound is myristyl nicotinate.

6. The method of claim 1, wherein said compound is a lauryl niacin ester.

7. A method for lowering serum LDL in a subject in need thereof comprising topically administering to said subject an amount of a compound of formula

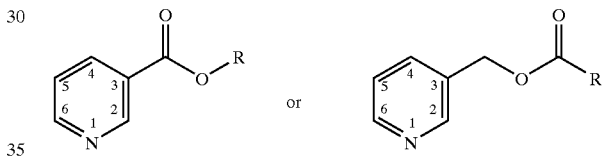

wherein in each compound R is C1–C22 alkyl, in an amount sufficient to reduce serum LDL in said subject.

8. The method of claim 7, wherein R is C10–C18 alkyl.

9. The method of claim 7, wherein said compound is

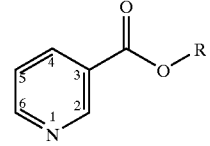

wherein R is C1–C22 alkyl.

10. The method of claim 7, wherein said compound is

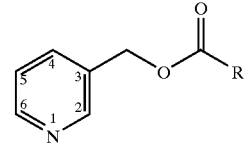

wherein R is C1–C22 alkyl.

11. The method of claim 7, wherein said compound is myristyl nicotinate.

12. The method of claim 7, wherein said compound is a lauryl niacin ester.

13. A method of increasing serum HDL levels in a subject in need thereof comprising topically administering to said subject an amount of a compound of formula

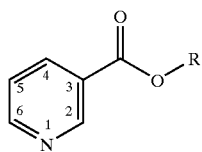 or 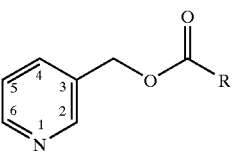

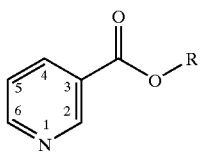 or 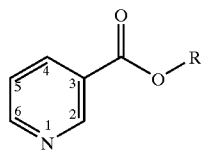

wherein in each compound R is C1–C22 alkyl, in an amount sufficient to raise serum HDL in said subject.

14. The method of claim 13, wherein R is C10–C18 alkyl.

15. The method of claim 13, wherein said compound is

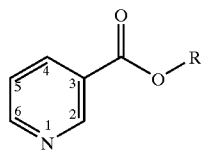

wherein R is C1–C22 alkyl.

16. The method of claim 13, wherein said compound is

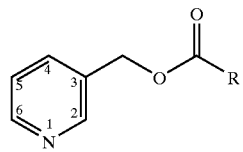

wherein R is C1–C22 alkyl.

17. A method of improving total cholesterol profile in a subject in need thereof comprising topically administering to said subject an amount of a compound of formula wherein in each compound R is C1–C22 alkyl, in an amount sufficient to (i) lower the ratio of total cholesterol: HDL, and/or (ii) lower the ratio of LDL:HDL in said subject.

18. The method of claim 17, wherein R is C10–C18 alkyl.

19. The method of claim 17, wherein said compound is

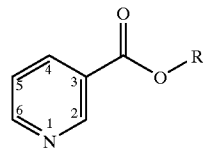

wherein R is C1–C22 alkyl.

20. The method of claim 17, wherein said compound is

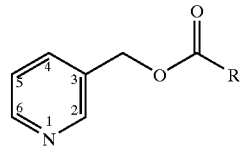

wherein R is C1–C22 alkyl.

* * * * *